(12) United States Patent
Sussman et al.

(10) Patent No.: US 6,918,281 B2
(45) Date of Patent: Jul. 19, 2005

(54) GAS SENSOR CALIBRATION SYSTEM

(75) Inventors: Michael Sussman, Verwood (GB); Charles Edward Downs, Wimbourne (GB); Tom Ford, Royston (GB); David Smith, Royston (GB)

(73) Assignee: Zellweger Analytics Limited, Poole (GB)

( * ) Notice: Subject to any disclaimer, the term of this patent is extended or adjusted under 35 U.S.C. 154(b) by 80 days.

(21) Appl. No.: 10/275,794

(22) PCT Filed: May 11, 2001

(86) PCT No.: PCT/GB01/02105

§ 371 (c)(1),
(2), (4) Date: Apr. 23, 2003

(87) PCT Pub. No.: WO01/86286

PCT Pub. Date: Nov. 15, 2001

(65) Prior Publication Data

US 2003/0167821 A1 Sep. 11, 2003

(30) Foreign Application Priority Data

May 11, 2000 (GB) .............................................. 0011391

(51) Int. Cl.⁷ .......................... G01N 37/00; G01N 27/26
(52) U.S. Cl. ........................... 73/1.06; 73/1.03; 73/1.05
(58) Field of Search ............................... 73/1.03–1.07; 436/9; 204/401, 427–429

(56) References Cited

U.S. PATENT DOCUMENTS

| | | | |
|---|---|---|---|
| 4,489,590 A | * 12/1984 | Hadden | 73/1.04 |
| 4,736,617 A | 4/1988 | Huhmer et al. | 73/23.2 |
| 4,854,153 A | 8/1989 | Miyagawa et al. | 73/1.06 |
| 4,882,576 A | 11/1989 | Boyd | 73/1.04 X |
| 4,944,861 A | * 7/1990 | Reber | 204/428 |
| 5,493,890 A | * 2/1996 | Dussault et al. | 73/1.06 |
| 5,665,894 A | 9/1997 | Baker | 73/1.05 |
| 5,969,223 A | * 10/1999 | Nagai et al. | 73/1.06 |
| 2004/0074279 A1 | * 4/2004 | Forrest | 73/1.06 |

FOREIGN PATENT DOCUMENTS

| | | | | |
|---|---|---|---|---|
| DE | 19708052 A | * 11/1997 | | G01N/37/00 |
| DE | 297 23 567 | 4/1999 | | G01N/37/00 |
| EP | 744 620 | 11/1996 | | G01N/33/00 |
| GB | 2049193 A | * 12/1980 | | A61B/5/18 |
| GB | 2392727 A | * 3/2004 | | G01N/33/00 |

* cited by examiner

*Primary Examiner*—Thomas P. Noland
(74) *Attorney, Agent, or Firm*—Andrus, Sceales, Starke & Sawall, LLP

(57) ABSTRACT

The present invention provides a method of calibrating sensors within a gas detector (36) having a housing containing a gas inlet whereby gas can diffuse from the inlet to the sensors. The gas inlet in the housing is held against part (34) of the calibration apparatus to form a sealed gas interface between the apparatus and the detector; a source (10) of pressurized calibration gas is connected to the apparatus, and a predetermined dose of calibration gas is delivered to the interface between the detector (36) and the calibration apparatus (34) at a predetermined pressure. The source (10) of pressurized calibration gas may contain single or multiple calibration doses and, if the former, the calibration apparatus includes a dosing system such as cylinder (14) for metering individual doses of calibration gas.

12 Claims, 5 Drawing Sheets

GAS SENSOR CALIBRATION SYSTEM

CROSS REFERENCE TO RELATED APPLICATION

The present application is the U.S. national stage application of International Application PCT/GB01/02105, filed May 11, 2001, which international application was published on Nov. 15, 2001 as International Publication WO 01/86286. The International Application claims priority of British Patent Application 0011391.0, filed May 11, 2000.

TECHNICAL FIELD

The present invention relates to a system for calibrating gas sensors, which are used in gas detectors or gas analyzers (the term "detector" will be used in this specification to cover both types of apparatus) to detect or analyse potentially hazardous environments, to ensure that the sensors provide accurate readings. The detector is generally of the type having a fluid inlet in contact with the atmosphere being monitored and having a diffusion path leading from the inlet to the or each gas sensor so that, in normal operation, gas present at the inlet diffuses to the or each sensor.

BACKGROUND ART

Portable gas detectors containing electrochemical gas sensors are well known for monitoring potentially hazardous environments, for example mines, tunnels, sewers and other closed environments. Safety regulations require that the sensors within the detector are tested on each occasion that they are taken into a potentially hazardous environment and calibrated according to manufacturer's recommendations and that is indeed good commercial practice but it is frequently not complied with for reasons of cost and time.

Currently, sensors are calibrated by passing a calibration gas of fixed, known composition from a gas bottle at a predetermined flow rate through a conduit and placing the sensor in contact with the gas flowing through the conduit. Calibration gas flowing out of the conduit is vented to atmosphere and so the procedure is wasteful of calibration gas, which is expensive. In addition, the gas flow rate in the conduit must be adjusted and controlled to pre-set levels, which is time consuming. For these reasons, calibration is often not performed as frequently as the regulations require. The gas required for calibration could be hazardous and if so, calibration should be carried out in a controlled environment.

GB-A-2049193 describes an alcohol meter that includes an arrangement for performing calibration by storing a calibration gas in a cylinder and pumping it past the sensor to the atmosphere. However, portable gas monitors that work by diffusion of the monitored gas into the monitor have no flow path past the sensor.

U.S. Pat. No. 4,489,590 describes a monitor for a flammable gas including a hood that isolates the monitor when calibration gas is applied.

U.S. Pat. No. 4,854,153 describes the calibration of a sensor by flowing calibration gas past the sensor The present invention provides an alternative, quicker and more cost effective method of calibrating gas sensors.

DISCLOSURE OF THE INVENTION

According to the present invention, there is provided an apparatus for calibrating at least one sensor within a gas detector having a gas inlet in fluid communication with the or each sensor, the apparatus comprising:

a holder for holding a gas detector with respect to the apparatus in such a manner that a region of the detector containing the gas inlet abuts against the apparatus to form a sealed gas interface between the apparatus and the detector;

a connector for connecting a source of pressurized calibration gas to the apparatus, and a conduit for delivering a predetermined dose of calibration gas from the connector to the interface between the detector and the apparatus.

The source of pressurized calibration gas may contain only enough calibration gas for a single calibration operation, i.e. the source provides a single "shot" of calibration gas. Alternatively, the source may be a bottle containing more than one dose, in which case the apparatus further includes a metering device for delivering a metered dose of calibration gas to the interface. Both these arrangements are quicker, easier, safer and less wasteful of calibration gas than the prior art arrangement and accordingly stand a better chance of being used on each occasion that the detector is used in a potentially hazardous space than the prior art arrangement described above. Because the arrangement of the present invention is much less wasteful of calibration gas, it is also more economic than the prior art arrangement.

Generally the gas detector has a cavity containing the sensor(s) and having an opening that is in contact with the atmosphere being sensed that allows gas from the atmosphere to diffuse through the opening into the cavity and hence to the sensors. Apart from the opening, the cavity is generally closed and so the cavity will generally have a predetermined (i.e. fixed) volume and the present invention achieves calibration by releasing a predetermined amount of gas (generally a predetermined volume at a predetermined pressure) into the cavity.

The present invention also provides a method of calibration using the above apparatus.

BRIEF DESCRIPTION OF THE DRAWINGS

Two forms of the apparatus according to the present invention will now be described, by way of example only, with reference to the accompanying drawings in which.

DETAILED INVENTION OF THE PRESENT INVENTION

Figure 1:
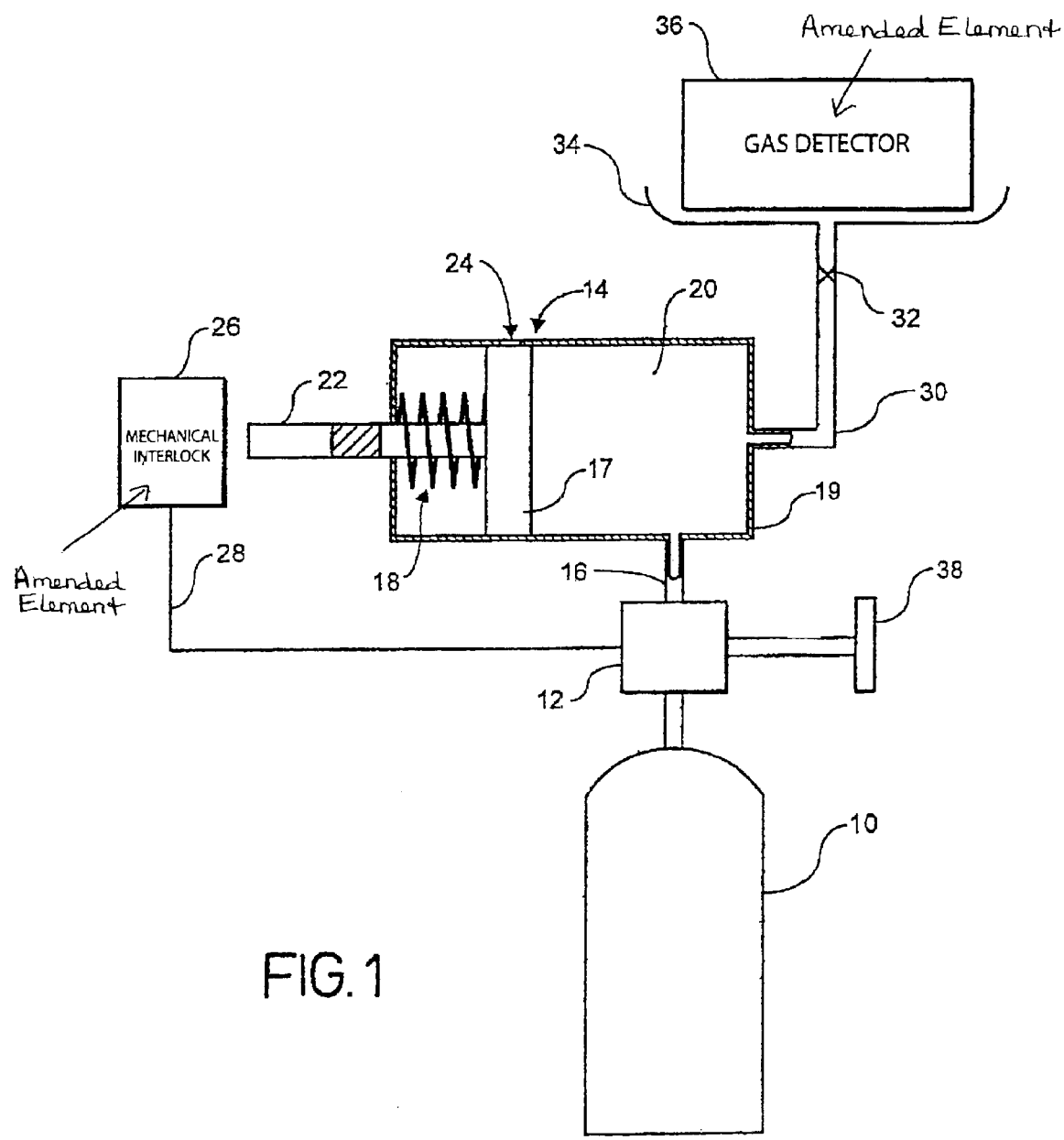
FIG. 1 is a schematic cross section through an apparatus of the present invention for providing metered doses of calibration gas from a gas cylinder.

Referring initially to FIG. 1, a gas bottle 10 containing enough pressurized calibration gas for several gas detector calibrations is connected to control valve 12, e.g. by way of a standard on/off valve and optionally a pressure reduction valve (not shown). The valve 12 is connected to a dosing system 14 by a conduit 16. The dosing system 14 includes a cylinder 19 and a piston 17 carried by piston rod 22 and operating within the cylinder 19. The piston 17 is urged by a spring 18 to the right (as seen in FIG. 1), forming a chamber 20 to the right of the piston in the cylinder. A pressure equalizing hole 24 is provided in the wall of the cylinder 19 that allows gas within the chamber 20 to escape when uncovered by piston 17, as will be described in more detail below.

A mechanical interlock 26 is triggered when engaged by the piston rod 22 and provides a signal to control valve 12 along a line 28. A further conduit 30 is provided that feeds gas from the chamber 20 to a holder 34 for holding a gas detector 36 during calibration. The conduit 30 includes a restrictor 32.

Figure 2:
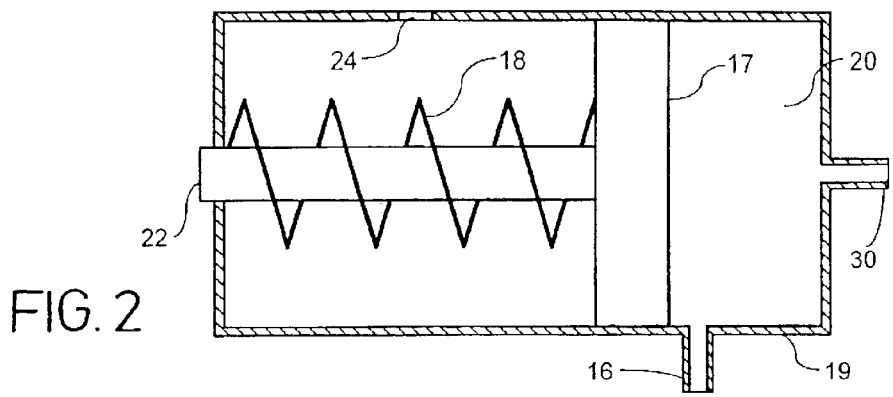
FIGS. 2–4 show the apparatus of FIG. 1 in various stages of delivering a predetermined dose of calibration gas.
Figure 3:
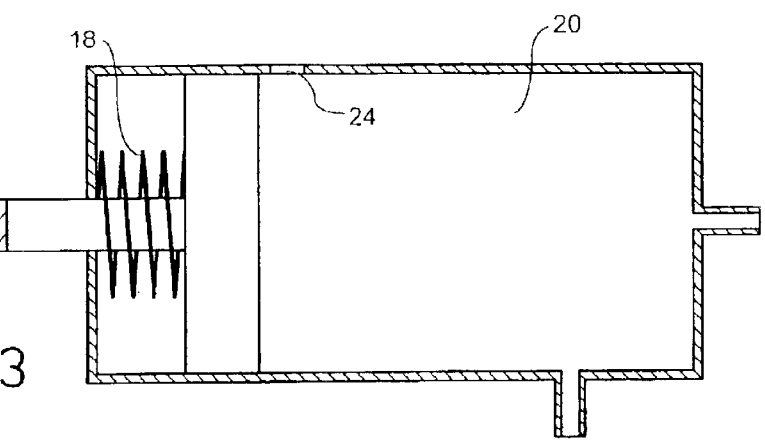

A push-button 38 is provided to initiate a calibration cycle. When pushed, button 38 opens the control valve 12 and allows gas from the gas bottle 10 to pass through the conduit 16 into the chamber 20 of the dosing system 14. When this occurs, the piston is in the position shown in FIG. 2; the gas entering the chamber 20 pushes the piston 17 to the left (as viewed in the Figures), thereby compressing the spring 18 as it does so. As the piston 17 is pushed to the left, it uncovers pressure equalizing hole 24. However, the rate at which gas escapes from the hole 24 is less than the rate at which gas enters the chamber 20 through the conduit 16. Accordingly, the piston 17 continues to be moved to the left until it engages the mechanical interlock 26. Interlock 26, when engaged by piston rod 22, sends the message along line 28 to the control valve 12, causing the valve to close. The position of the piston 17 at this point is shown in FIG. 3.

Figure 4:
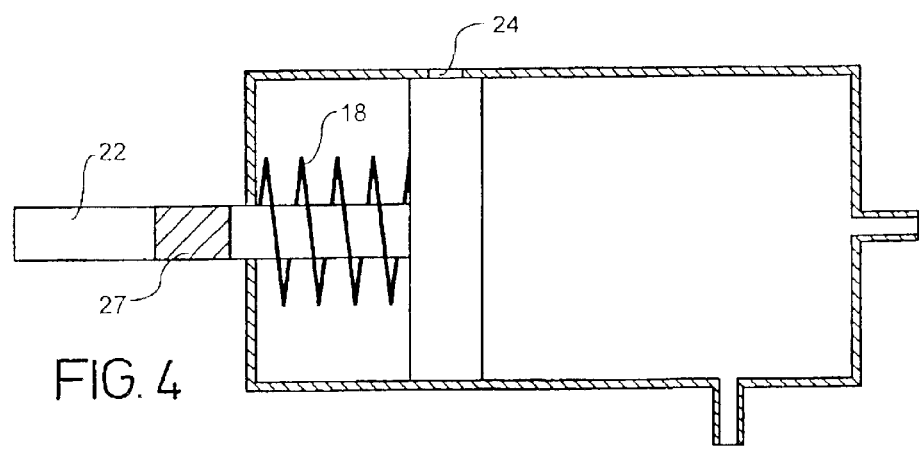

Gas escapes through hole 24, thereby allowing the spring 18 to push the piston 17 to the right until the piston covers the hole 24. This metering device 14 therefore provides a pre-set dose of gas at a pressure dictated by the value of the spring 18. The arrangement when the hole 24 is just covered by the piston is shown in FIG. 4. The interlock 26 can be placed directly behind the piston rod 22 so that only a small amount of gas escapes through hole 24 so that the amount of gas vented to atmosphere is very small.

A mark 27 is provided on the piston rod 22 that lines up with the end of the cylinder 19 to show that the correct dose is present. Typically, the chamber 20 contains approximately 50 $cm^3$ of the calibration gas at approximately 2 bars.

Gas within the chamber 20 is kept pressurized by spring 18 acting on the piston 17 so urging the gas to migrate through the restrictor 32 into the holder 34. The detector 36 is held by the holder in such a way that the conduit 30 provides calibration gas to the gas sensor(s) within the detector. The holder 34 maintains a gas seal between the detector and the holder so that all the gas passing through the restrictor 32 reaches the gas sensor(s). In this way, a pre-determined dose of gas is applied to the sensor(s) in the gas detector, which can be used for calibration. If the detector contains more than one sensor, it is convenient that the calibration gas is a mixture of the gases to which the sensors respond.

Figure 5:
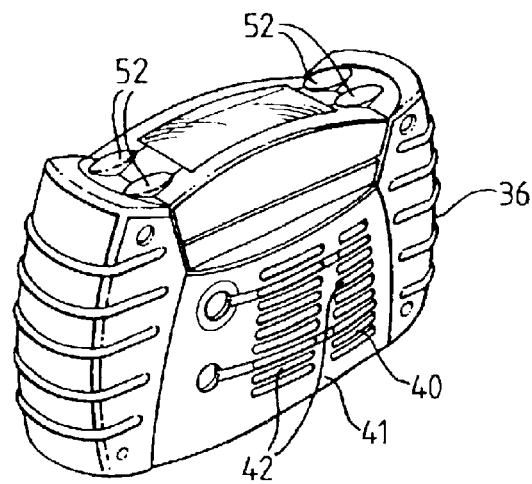
FIGS. 5 to 8 are perspective views of two forms of apparatus showing the attachment between a gas detector and the apparatus of the present invention.
Figure 5:
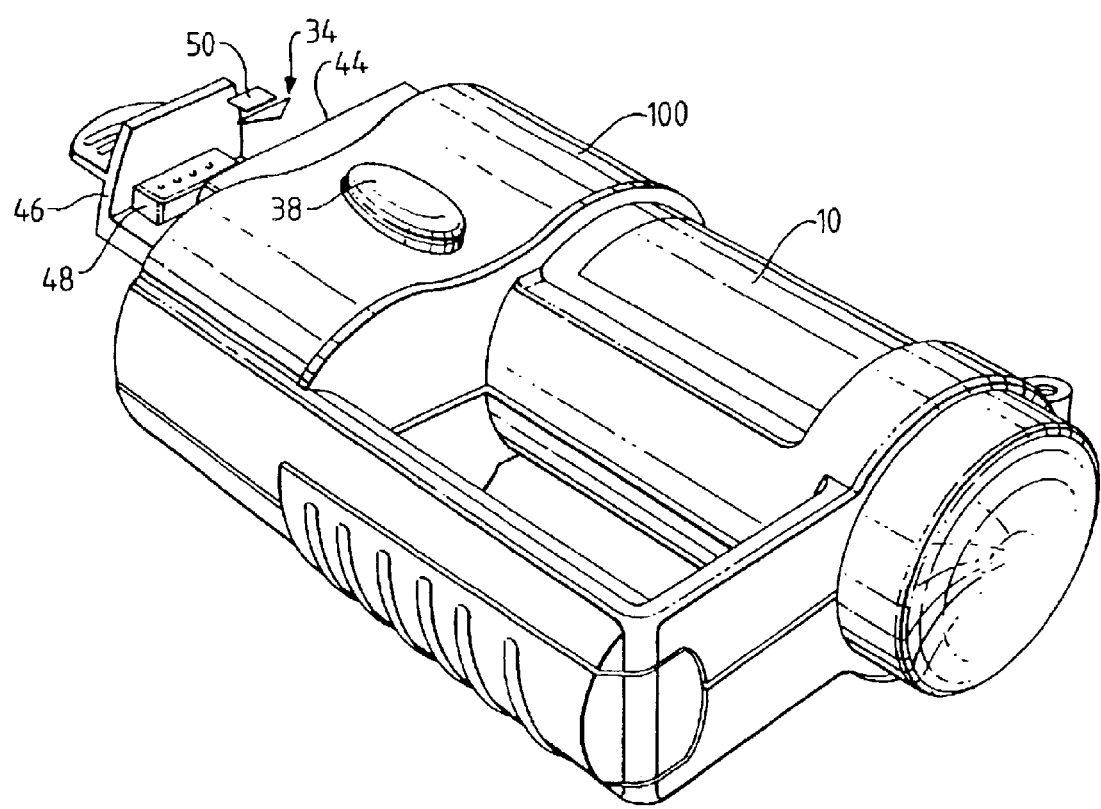
Figure 6:
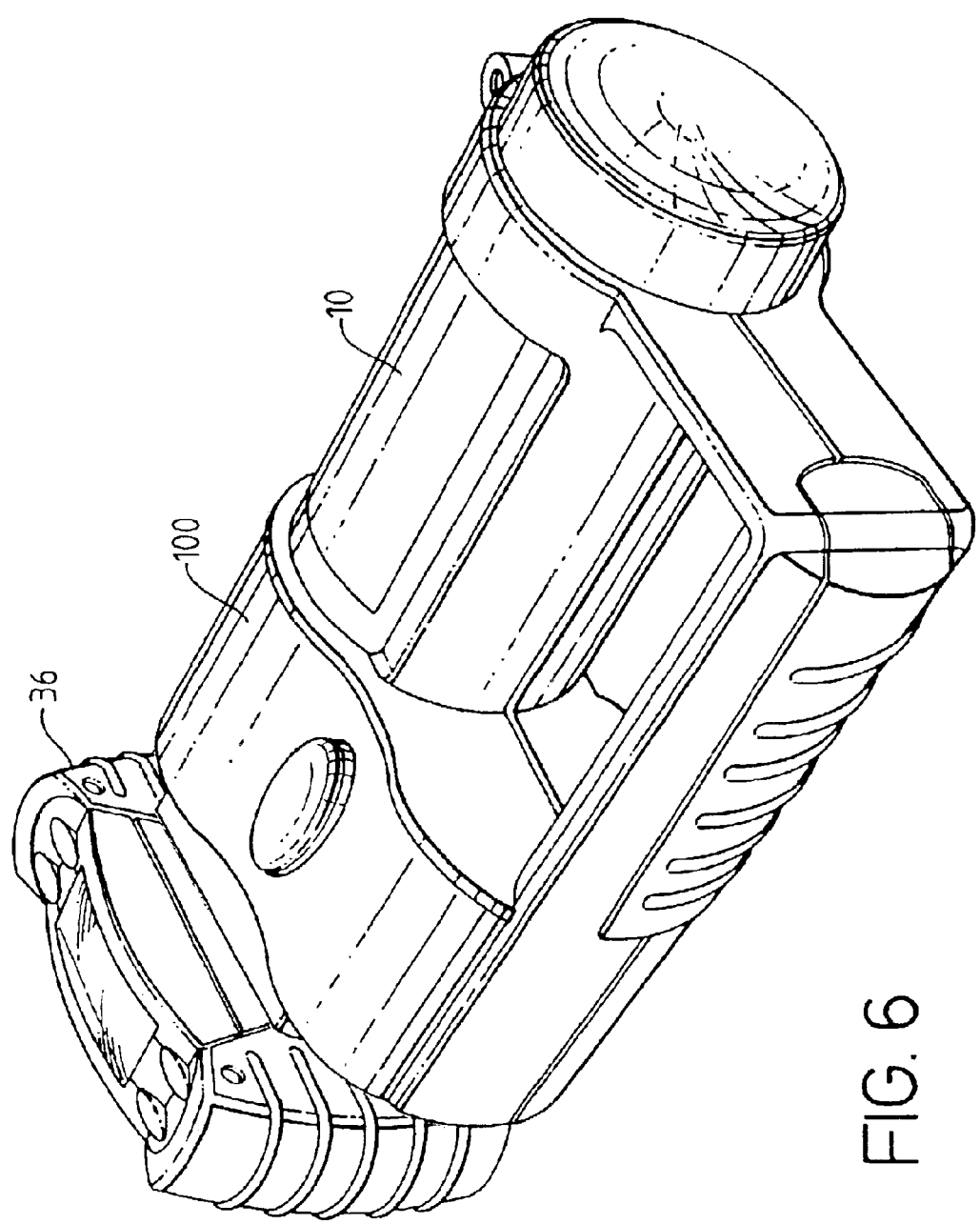

FIGS. 5 and 6 are isometric views of the apparatus shown schematically in FIG. 1. The apparatus has a housing 100 containing the gas dosing system 12 to 32. A gas bottle 10 containing, for example, 10 litres of calibration gas at approximately 10 bar is secured within the housing 100. The push button 38 used to initiate the calibration process is also shown. A detector 36 is shown that fits onto a holder 34 consisting of an "L"-shaped slider element 46 and electrical connections 48, which allow electrical signals to pass between the calibration apparatus and the detector 36, e.g. to initiate calibration. The detector 36 is fitted into the holder 34, which is then moved in the direction of arrow 50, e.g. by spring (not shown) so as to hold the front face 41 of the gas detector 36 against the end face 44 of the housing 100 to form a seal between the two parts. The gas detector 36 has openings 42 to allow gas to reach the sensors within the detector (the sensors as not shown). The gas flowing through the conduit 30 is fed into the interface between the housing and the gas inlets 42 are also in contact with this interface, thereby allowing the gas to reach the sensor(s). Because there is a seal around the front face 41, the calibration gas cannot escape when it passes from conduit 30 into the gas detector 36.

The gas detector 36 also includes an alarm loud speaker behind grill 40 and control buttons 52 and screen to control the function of the gas detector, including switching it into calibration mode.

FIG. 6 shows the arrangement when the gas detector 36 is fitted onto the holder 34.

Figure 7:
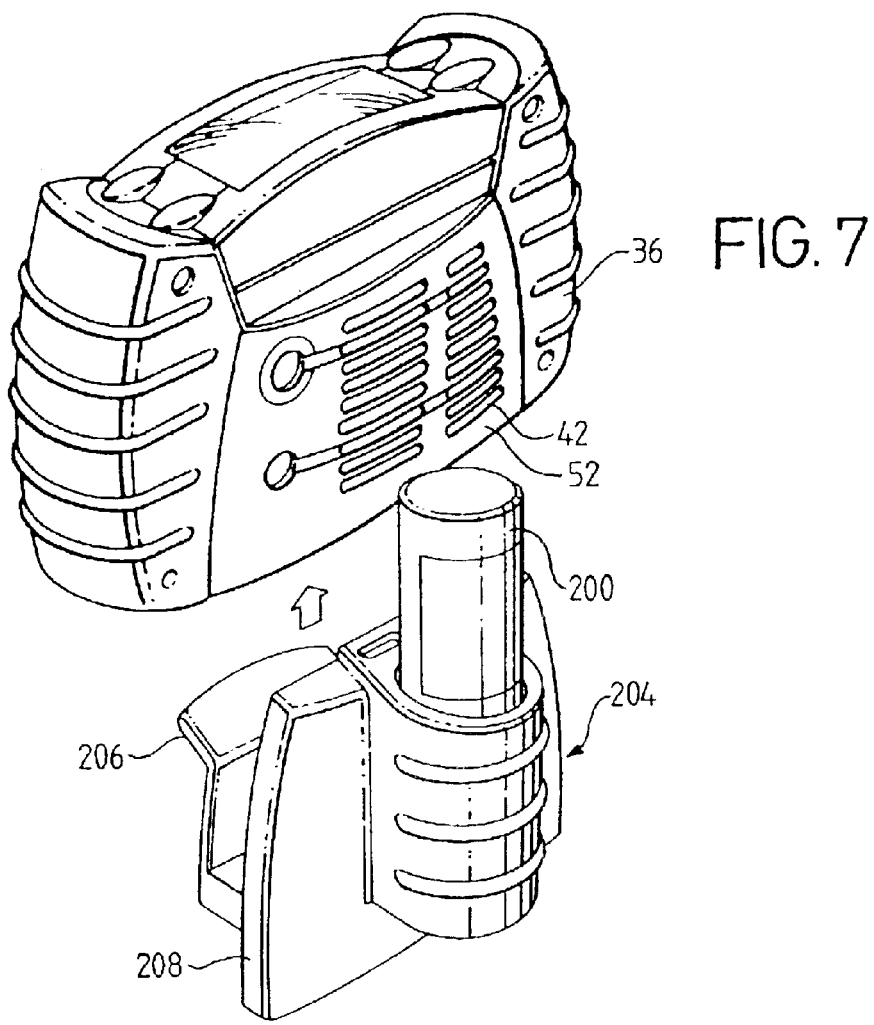
Figure 8:
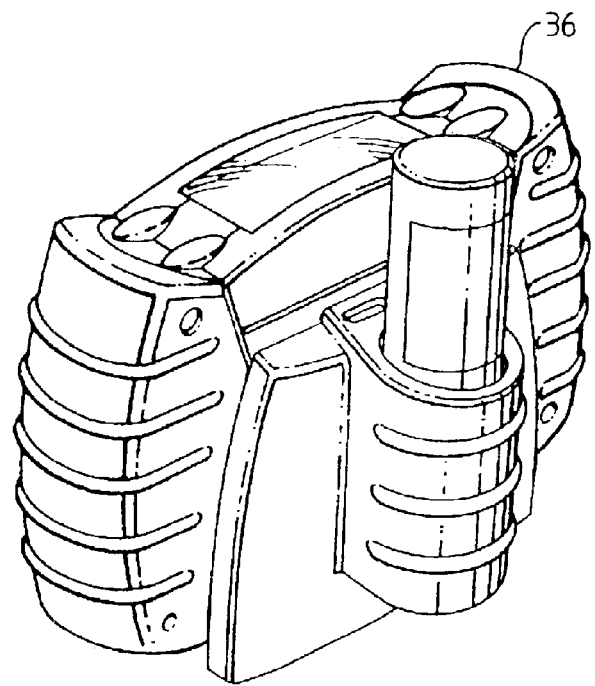

FIGS. 7 and 8 show an alternative arrangement in which a single-shot gas bottle 200 is provided which fits into a holder 204 that clips onto the front of the gas detector 36. The detector is held onto the holder by means of a spring clip 206. This arrangement does not require a dosing system, as described in connection with FIGS. 1 to 4, since each gas bottle contains the exact amount of gas to provide a single calibration. The gas bottle 200 fits into a socket 202 in the holder, at the base of which is a hollow pin (not shown) which perforates a seal on the gas bottle 200 and conducts calibration gas to interface between the holder and the detector 36, from where it passes into the gas inlets 42 of the gas detector 36.

When it is required to calibrate the gas detector 36, it is clipped onto the holder 204 and the spring clip 206 forms a seal between the front face 52 of the detector 36 and the front plate 208 of the holder. A gas bottle 200 is then inserted into the socket in the holder and pressed down to push the hollow needle into the seal of the gas bottle 200, where upon a single dose of calibration gas is released to the interface between the plate 208 and the detector and from there into the detector 36 for calibration. Once calibration has been completed, the gas bottle 200 can be removed from the socket 202 and thrown away.

FIG. 8 shows the arrangement when the gas detector 36 is fitted onto the holder 204.

What is claimed is:

1. An apparatus for calibrating at least one sensor within a gas detector having a gas inlet in fluid communication with the or each sensor, the apparatus comprising:
   a holder for holding a gas detector with respect to the apparatus in such a manner that a region of the detector containing the gas inlet of the detector abuts against the apparatus to form a gas interface between the apparatus and the detector that is essentially sealed from the ambient atmosphere;
   a connector for connecting a source of pressurized calibration gas to the apparatus; and
   a gas delivery system arranged to deliver a pre-metered dose of calibration gas to the interface between the detector and the apparatus at a predetermined pressure.

2. The apparatus of claim 1, which includes a source of calibration gas, which contains a single calibration dosage.

3. The apparatus of claim 1, which includes means for metering individual doses of calibration gas to sensors within the detector.

4. The apparatus of claim 3, which includes a source of calibration gas containing two or more calibration dosages.

5. The apparatus of claim 1, which includes a detector containing at least one gas sensor.

6. The apparatus of claim 5, wherein the detector is of the type in which the fluid inlet of the detector is in contact with the at least one sensor by a diffusion path and, in normal operation, gas present at the inlet in operation diffuses to the at least one sensor.

7. The apparatus of claim 5, wherein the at least one gas sensor is an electrochemical gas sensor.

8. A method of calibrating at least one sensor within a gas detector having a gas inlet in fluid communication with the at least one sensor, the method comprising:

holding a region of the detector containing the gas inlet against a calibration apparatus to form a gas interface between the apparatus and the detector that is essentially sealed from the ambient atmosphere;

connecting a source of pressurized calibration gas to the apparatus; and delivering a pre-metered dose of calibration gas to the interface between the detector and the apparatus at a predetermined pressure.

9. The method of claim 8 wherein the detector is of the type in which the fluid inlet of the detector is in contact with the at least one sensor by a diffusion path and, in normal operation, gas present at the inlet in operation diffuses to the at least one sensor.

10. The method of claim 9 wherein the source of pressurized gas includes more than one predetermined dose of calibration gas and the method comprises metering individual doses of calibration gas from the source prior to delivering the dose to sensors within the detector.

11. The method of claim 8 wherein the source of pressurized gas includes more than one predetermined dose of calibration gas and the method comprises metering individual doses of calibration gas from the source prior to delivering the dose to sensors within the detector.

12. An apparatus for calibrating at least one sensor within a gas detector having a gas inlet in fluid communication with the at least one sensor, the apparatus comprising:

a holder for holding a gas detector with respect to the apparatus in such a manner that a region of the detector containing the gas inlet of the detector abuts against the apparatus to form a sealed gas interface between the apparatus and the detector;

a connector for connecting a source of pressurized calibration gas to the apparatus; and a gas delivery system arranged to collect a pre-metered dose of calibration gas and subsequently deliver the collected pre-metered dose of calibration gas to the interface between the detector and the apparatus at a predetermined pressure.

* * * * *